United States Patent [19]

Comparetto

[11] 4,433,681
[45] Feb. 28, 1984

[54] BONE ELONGATION OR SHORTENING METHOD

[76] Inventor: John E. Comparetto, P.O. Box 433, Nassawadox, Va. 23413

[21] Appl. No.: 280,977

[22] Filed: Jul. 7, 1981

Related U.S. Application Data

[63] Continuation of Ser. No. 32,310, Apr. 23, 1979, abandoned, which is a continuation-in-part of Ser. No. 763,623, Jan. 28, 1977, Pat. No. 4,150,675.

[51] Int. Cl.³ .............................................. A61F 5/04
[52] U.S. Cl. ................................ 128/92 E; 128/305; 128/92 R; 128/92 G; 128/303 R
[58] Field of Search ............... 128/92 E, 92 R, 305, 128/303 R, 84 R, 42 G; 30/358, 277, 305, 301, 302, 303 R, 314, 315, 316; 144/85, 86, 88, 309 L

[56] References Cited

U.S. PATENT DOCUMENTS

| | | | |
|---|---|---|---|
| 13,574 | 9/1855 | Hughes | 144/85 |
| 109,675 | 11/1870 | Schmid | 144/88 |
| 339,700 | 4/1886 | Schmid | 144/88 |
| 593,386 | 11/1897 | Williams | 30/316 X |
| 4,150,675 | 4/1979 | Comparetto | 128/305 |

*Primary Examiner*—C. Fred Rosenbaum
*Assistant Examiner*—C. W. Shedd

[57] ABSTRACT

Bones are cut in parallel curvilinear cuts and are elongated or shortened or angularly adjusted with the curvilinear curse wedged together for strength. Excised parts are used to build up the cut parts. A blade or guide has a ribbon shape with opposite flanges, neck, pre-neck and loop regions. One blade or guide has additional slide blade or guides to perform double cuts.

7 Claims, 10 Drawing Figures

BONE ELONGATION OR SHORTENING METHOD

This is a continuation of application, Ser. No. 32,310, filed Apr. 23, 1979, now abandoned, which was a continuation-in-part of copending application Ser. No. 763,623, filed Jan. 28, 1977, now U.S. Pat. No. 4,150,785.

BACKGROUND OF THE INVENTION

Shortening of bones has been done utilizing various cutting means to perform a "step down" osteotomy. The same type of osteotomy is used for lengthening bones but is accomplished in an incremental manner of approximately 1 mm per day in a framelike device that slowly moves the osteotomy.

The step down osteotomy is as follows: a cut is made in a bone, then second cuts are made removing sections of bone. The bone is then moved in, thus filling the spaces of the removed bone. The elongation procedure is the same but without the second cuts, followed by moving and pinning grafts are often necessary.

Opposite half transverse cuts are joined by a lateral longitudinal cut. Ends are slid apart along the axial cut at an elongation rate of 1 mm per day. Shortening requires parallel half transverse cuts and removal of bone pieces between the adjacent cuts.

SUMMARY OF THE INVENTION

Bones are cut in parallel curvilinear cuts with curvilinear double cutters. Curvilinear kerfs are wedged together for strength. Excised parts are used to build up the cut parts.

One object of the invention is the provision of a bone length-changing procedure having steps of cutting across and severing parts of a bone with a ribbon-shaped cut having a wedge-shaped portion, removing parts of the bone adjacent the cut relatively longitudinally moving the severed parts of a bone and stabilizing the bone for repair growth.

Another object of the invention is the provision of procedure for removing bone portions from lateral portions adjacent the wedge-shaped portions.

Another object of the invention is the procedure of cutting across and severing bone with ribbon-shaped cuts and forming flange, neck, pre-nect and loop regions of the cut on the bone.

Another object of the invention is the provision of the procedure of bone shortening by cutting similar ribbon-shaped cuts having bone flange, neck, pre-neck and male loop projections and female loop recept portions.

Still another object of the invention is the procedure of wedging a wedge-shaped portion of a first ribbon-shaped cut into a wedge-shaped portion of a second ribbon-shaped cut and wedging severed parts of a bone into gaps between flange, neck, pre-neck and loop regions of the two cuts.

A further object of the invention is an osteological knife having a ribbon-shaped, thin blade with a medial wedge-shaped portion with a first sharpened edge and means for applying force to the blade to drive the sharpened edge and ribbon-shaped blade transversely through a bone.

Yet another object of the invention is a knife having two ribbon-shaped, thin blades along flange and neck regions of a wedge-shaped portion.

Another object of the invention is a scoop area between the two ribbon-shaped, thin blades which collects severed parts of a bone.

A still further object of the invention is the provision of a device for bone-cutting that comprises a lobated or U-shaped structure with narrowed neck and two lateral flanges for the cutting of said shape in long bones.

DETAILED DESCRIPTION OF THE DRAWINGS

Using various size osteotomes of a ribbon-shaped configuration, ostectomies and osteotomies are accomplished that either elongate or shorten a bone.

Figure 1:
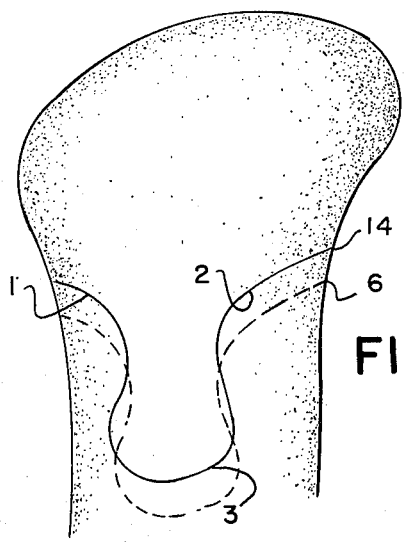
FIG. 1 is a schematic representation of cuts in a long bone according to the invention.
Figure 2:
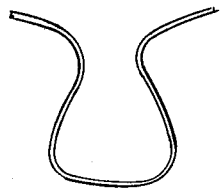
FIGS. 2-4 are details of cuts in a long bone according to the invention.
Figure 4:
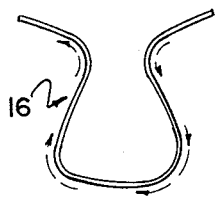

For bone shortening as shown in FIG. 1 ostectomies 1, 2 and 3 may be made by ribbon cuts of the same exact shape and size; either cut 4 or cut 6 can be made first with the osteotome shown in FIG. 2 or guide shown in FIG. 4. Bone pieces 1, 2 and 3 must be removed, then the site closed.

Bone elongation must be made with ribbon cuts of different sizes first cut with small ribbon second cut with larger ribbon.

The difference of size will be a function of the amount of elongation. The loop of the smaller ribbon cut must not be smaller than the neck of the larger ribbon cut. Lengthening may be precisely judged or determined by choosing a smaller ribbon loop diameter 8 to correspond to a specific diameter of a larger loop 11 and pre-neck region 10. Flanges of both 12 and 14 respectively must clear the sides of the bone.

Ribbon 16 are rigid structures such as metal that serve as guides for "dot" laser as in bone wedge osteotomies of the previous invention or the ribbons themselves might be fashioned of fiberoptic laser heads, etc.

At the end of the laser dot's journey, it triggers photoelectric shut-off in the elevator-retractor of previous invention.

Bone elongation is accomplished by placing traction on bone parts with subsequent wedging effect.

Figure 6:
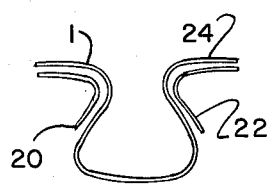
FIGS. 6 and 7 are representations of a cutter.
Figure 5:
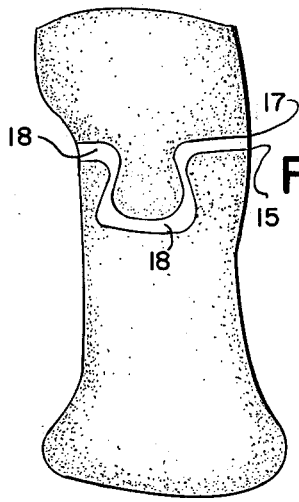
FIG. 5 is a schematic representation of bone elongation.

Referring to FIGS. 5 and 6, cut 15 and cut 17 may be made simultaneously by a double blade 23. The bone 18 between is removed with a blade removal device.

Bone within blades 23 can be used as bone matrix or wedges to help the elongation at any or all points marked with an 18 in FIG. 5 above.

Figure 3:
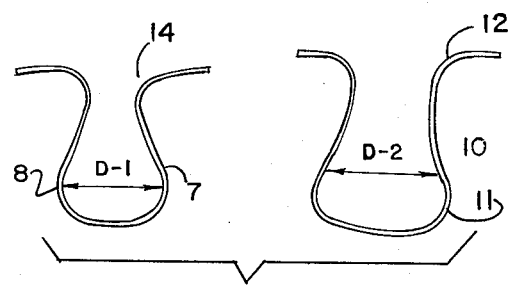
Figure 7:
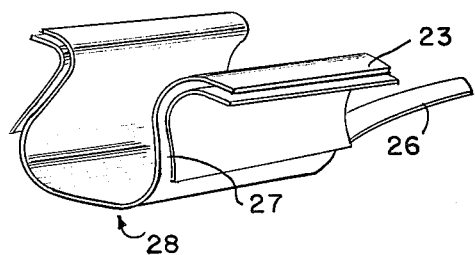

Another blade configuration is shown in FIG. 6 and FIG. 7 wherein points 20 and 22 respectively correspond to pre-neck 10 in FIG. 3 for making elongation 7. Area 24 of FIG. 6 corresponds to osteotomy (removal of bone). Handle 26 is connected to blades 27 and 28.

Figure 8:
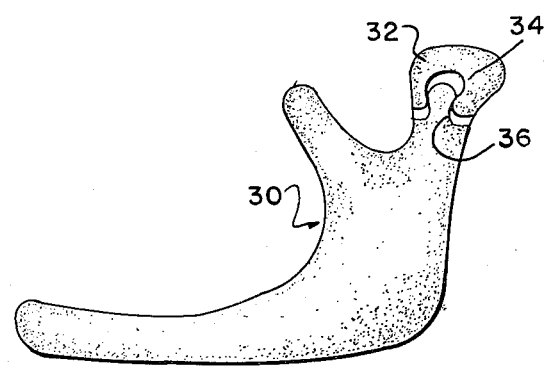
FIGS. 8-10 are representations of human mandible adjustment.
Figure 9:
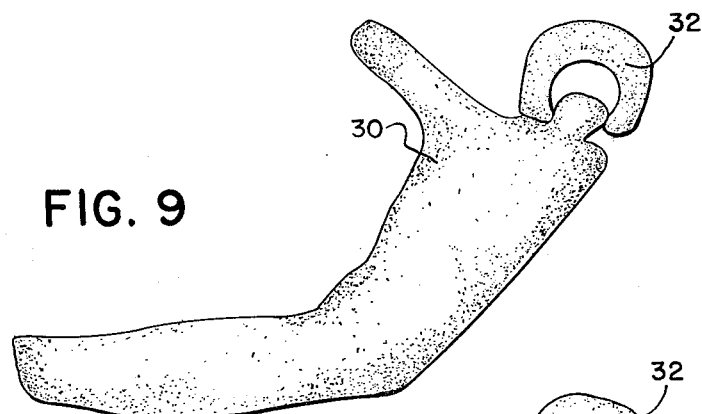

FIGS. 8 and 9 depict the human mandible. FIG. 8 illustrates a cut in the mandible superior to the mandibular nerve but inferior to the mandibular condyle 32.

FIG. 8 shows an even longitudinal lengthening and wedging of the mandibular bone by cuts 34 and 36. This same figure could depict shortening of the bone as well. Incremental lengthening is seldom necessary in this instance since the angulation and entry of the mandibular nerve is out of harm's way from the lengthening procedure depicted.

FIG. 9 shows a lengthening or shortening procedure where there is either a forward anterior or inferior movement of the mandible until wedging occurs at "X" points.

Figure 10:
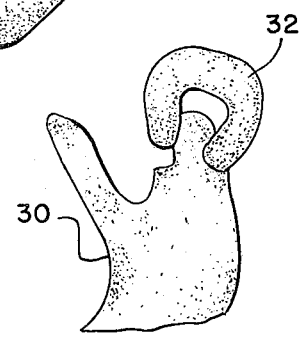

FIG. 10 shows a similar procedure as in FIG. 9, however, here rotation is in the opposite direction with different areas of wedging ("X"'s).

What is claimed is:

1. A corrective surgical procedure which corrects or improves upon an imperfection in a deformed living long bone which procedure comprises the steps of:
   (a) Surgically exposing thhe deformed bone at an operative site auspicious for corrective surgery,
   (b) cutting said deformed bone so as to sever same and thereby form a loosely interlocking dove-tail joint in adjacent osseous tissue of said long bone at said site,
   (c) correctively reorienting the relative position of the interlocked adjacent parts of said surgically severed long bone within the limits of said loosely interlocking dovetail-like joint,
   (d) stabilizing said severed long bone in said reoriented corrective position,
   (e) closing said operative site in a manner conducive to tissue regrowth,
   (f) wherein said step of severing further includes producing multiple curvalinear cuts which each have a cross section substantially in the shape of the capital Greek letter omega ($\Omega$) whereby said interlocking dovetail-like joint is formed by said curvilinear cuts.

2. The procedure of claim 1 wherein the step of reorienting comprises relative elongation of said bone.

3. The procedure of claim 1 wherein the step of reorienting comprises relative axial rotation of severed bone sections.

4. The procedure of claim 1 wherein the reorienting step comprises relative shortening of said bone.

5. The procedure of any one of claims 1, 2, 3, or 4 wherein said step of stabilizing further includes recovering bone tissue removed from said bone during the step of making multiple transverse curvilinear cuts and inserting said recovered tissue into any voids which persist in the loosely interlocking dovetail-like joint after said adjacent bone parts have been correctively reoriented so as to promote faster healing of the surgically altered long bone.

6. The procedure of claim 1 wherein the step of cutting is performed using an osteotome which has been formed to have a cross section substantially in the shape of the capital greek letter omega ($\Omega$).

7. The procedure of claim 1 wherein the step of cutting is performed using laser means for producing said curvalinear cuts.

* * * * *